United States Patent
Korth et al.

(10) Patent No.: US 7,906,290 B2
(45) Date of Patent: Mar. 15, 2011

(54) ANTIBODY FOR DIAGNOSING NEUROPSYCHIATRIC DISEASES, IN PARTICULAR SCHIZOPHRENIA, DEPRESSION AND BIPOLAR AFFECTIVE DISORDERS

(75) Inventors: Carsten Korth, Dusseldorf (DE); S. Rutger Leliveld, Dusseldorf (DE)

(73) Assignee: Carsten Korth, Düsseldorf (DE)

( * ) Notice: Subject to any disclaimer, the term of this patent is extended or adjusted under 35 U.S.C. 154(b) by 1222 days.

(21) Appl. No.: 10/597,905

(22) PCT Filed: Feb. 11, 2005

(86) PCT No.: PCT/EP2005/001371
§ 371 (c)(1), (2), (4) Date: Aug. 11, 2006

(87) PCT Pub. No.: WO2005/077978
PCT Pub. Date: Aug. 25, 2005

(65) Prior Publication Data
US 2008/0286197 A1   Nov. 20, 2008

(30) Foreign Application Priority Data
Feb. 13, 2004 (DE) .................. 10 2004 007 462

(51) Int. Cl.
G01N 33/53 (2006.01)
G01N 33/533 (2006.01)
G01N 33/534 (2006.01)
G01N 33/561 (2006.01)
G01N 33/567 (2006.01)
C12P 21/08 (2006.01)
C07K 16/18 (2006.01)
A61K 49/16 (2006.01)
A61B 5/055 (2006.01)

(52) U.S. Cl. ........ 435/7.1; 435/7.21; 435/7.92; 435/7.95; 530/388.1; 530/387.1; 530/387.3; 424/9.1; 424/9.34

(58) Field of Classification Search .................. None
See application file for complete search history.

(56) References Cited

FOREIGN PATENT DOCUMENTS

| WO | 00/26675 | | 5/2000 |
|---|---|---|---|
| WO | WO 00/26675 | * | 5/2000 |
| WO | WO 2005/019828 A1 | * | 3/2005 |

OTHER PUBLICATIONS

Alberts B et al. Molecular Biology of the Cell, Third Edition. 2002. pp. 1216-1220.*
Kuby J. Immunology, Third Edition. WH Freeman & Co., New York, 1997. pp. 131-134.*
Wall CA et al. Psychiatric manifestations of Creutzfeldt-Jakob disease: A 25-year analysis. J Neuropsychiatry Clin Neurosci. 2005; 17(4):489-95.*
Amanda J. Law et al.; The distribution and morphology of prefrontal cortex pyramidal neurons identified using anti-neufilament antibodies SMI32, N200 and FNP7. Normative data and a comparison in subjects schizophrenia, bipolar disorder or major depression; Journal of Psychiatric Research; vol. 37, No. 6, Nov. 6, 2003; pp. 487-499; XP002348495.
Hans-Gert Bernstein et al.; "Increased number of nitric oxide synthase immunoreactive Purkinje cells and dentate nucleus neurons in schizophrenia"; Journal of Neurocytology; vol. 30, No. 8; Aug. 8, 2001; pp. 661-670; XP002348496.
William G. Honer et al.; "Monoclonal antibodies to study the brain in schizophrenia"; Brain Research, vol. 500, No. 1-2; 1989; pp. 379-383; XP00238497.
Einar M. Sigurdsson et al.; "Anti-prion antibodies for prophylaxis following prion exposure in mice"; Neuroscience Letters, Limerick, IE, vol. 336, No. 3; Jan. 23, 2003; pp. 185-187; XP002275536.
Carsten Korth et al.; "Monoclonal Antibodies Specific for the Native, Disease-Associated Isoform of the Prion Protein"; Methods in Enzymology; Academic Press, Inc.; San Diego, CA, US; vol. 309; 1999; pp. 106-122; XP001104847.

* cited by examiner

*Primary Examiner* — Daniel E Kolker
*Assistant Examiner* — Kimberly A. Ballard
(74) *Attorney, Agent, or Firm* — Rankin, Hill & Clark LLP (57) ABSTRACT

An antibody for diagnosis or treatment of neuropsychiatric diseases, in particular schizophrenia, depression or bipolar affective disorders, is characterized in that the antibody recognizes misfolded specific proteins that can be assigned to one of the diseases, and a method for diagnosis by means of antibodies that bind to neuropsychiatric disease-specific proteins.

16 Claims, 7 Drawing Sheets

ANTIBODY FOR DIAGNOSING NEUROPSYCHIATRIC DISEASES, IN PARTICULAR SCHIZOPHRENIA, DEPRESSION AND BIPOLAR AFFECTIVE DISORDERS

This application is a national stage filing pursuant to 35 U.S.C. 371 of PCT/EP05/01371, having an International filing date of Feb. 11, 2005 and claiming the benefit of priority from the German patent application DE 10 2004 007 462.3, filed Feb. 13, 2004, all of which are incorporated by reference. The present application claims the benefit of these prior applications, including the right to priority.

BACKGROUND OF THE INVENTION

The present invention relates to antibodies for diagnosis and treatment of neuropsychiatric diseases. The invention essentially relates to neuropsychiatric diseases, such as schizophrenia, depression or bipolar affective disorders. The present application focuses essentially on schizophrenia. However, the statements thus made also pertain generally to other neuropsychiatric diseases.

Schizophrenia is a neuropsychiatric disease likely to have heterogeneous causes. From studies on twins it has meanwhile become accepted that biological causes are responsible for the development of schizophrenia. In terms of neuropathology, patients with schizophrenia are characterized by an expansion of the third cerebral ventricle which is considered to be an unspecific sign of a loss of brain structure. Schizophrenia, at least one sub-group of schizophrenia, namely those with pronounced so-called negative symptoms, can be classified amongst the neurodegenerative diseases (J. Lieberman 1999, Biological Psychiatry 46: 729f).

To date, no diagnosis of schizophrenia or other neuropsychiatric diseases can be made on the basis of biological criteria. In order to determine a diagnosis, suitably trained physicians (psychiatrists, neurologists) interview for certain main psychiatric symptoms; this can be made more objective by means of so-called check lists. Unlike diseases in the area of internal medicine or neurology, the disease cannot be diagnosed by means of unambiguous blood or liquor tests or imaging procedures. This leads to some uncertainty in determining the diagnosis.

From WO 0026675 a generic method for diagnosis of neuropsychiatric diseases is known, in which the presence of polyglutamine-containing proteins in a tissue or body fluid sample of a patient is tested by means of an antibody that is directed against polyglutamine-containing protein domains. Further, WO 0026675 specifies that the neuropsychiatric diseases to be diagnosed with this method can be schizophrenia.

Polyglutamine-containing proteins are present in a plurality of neurodegenerative diseases, e.g. Huntington's disease or spinocerebellar ataxias. These diseases are characterized by increased occurrence of repeating glutamine residues in one or more proteins due to mutation, and are also referred to collectively as CAG repeat diseases since the DNA triplet, CAG, codes for glutamine.

In this context, for example, in Huntington's disease, a mutation in the human HD gene leads to an increase in the number of glutamine residues at the N-terminus of the huntingtin protein. Because of its erroneous amino acid sequence, the polyglutamine-rich mutant huntingtin tends to aggregate with other polyglutamine-rich huntingtin molecules. In the process, agglomerates are formed in the cellular nucleus of neurons that are associated with the fatal course of the disease. Similar sequence-related protein aggregations are thought to be responsible for the generation of disease-specific symptoms of other polyglutamine diseases.

The method known from WO 0026675 uses a monoclonal antibody (1C2) that is directed against polyglutamine-containing protein domains and is therefore not specific for schizophrenia. The method is only suitable for detecting polyglutamine-containing proteins. However, there is some doubt as to whether or not schizophrenia is even associated with the occurrence of polyglutamine-containing proteins. These doubts shall be elaborated in more detail below.

On the presumption—postulated in WO 0026675, but nevertheless incorrect—that schizophrenia is associated with the presence of polyglutamine-containing proteins, the known method could, thus, help in supporting a suspicion of schizophrenia that is based on a psychiatric diagnosis. However, diagnosis of schizophrenia through the use of this method alone is not feasible.

BRIEF SUMMARY OF THE INVENTION

It is the object of the present invention to provide antibodies for diagnosis or treatment of neuropsychiatric diseases, in particular of schizophrenia, depression or bipolar affective disorders. Further, it is an object of the present invention to provide a method that can be used to reliably and unambiguously diagnose said neuropsychiatric diseases, in particular schizophrenia. And lastly, it is another object of the present invention to provide pharmaceutical compositions for treatment of, for example, schizophrenia.

According to the invention, an antibody is provided that generally recognizes misfolded proteins that can be assigned to a neuropsychiatric disease. Preferably, antibodies recognizing misfolded proteins that are specific for schizophrenia, depression or bipolar affective disorders are provided.

For the purposes of the invention, the term "neuropsychiatric disease" shall cover in particular psychoses, including organic psychoses, i.e. diseases comprising classical features of psychosis as symptoms (delusion, hallucinations, impairment of thought, mood changes or other affective symptoms and cognitive disorders). It is particularly preferred for this to concern schizophrenia, depression, and bipolar disorders.

In a further development, it is also conceivable that an antibody according to the invention recognizes misfolded proteins that are specific for multiple neuropsychiatric diseases, whereby the assignment to a disease is possible by means of further properties of the protein, for example, its solubility or its molecular weight, or by means of the origin of the protein, for example, from a certain region of the brain.

A preferred development provides the antibody according to the invention to be obtained by immunization of suitable animals with purified brain fractions of patients afflicted by a neuropsychiatric disease, whereby steps are provided in the purification that effect an enrichment of misfolded proteins.

In order to illustrate the antibody according to the invention in more detail, it is necessary to first refer again to the polyglutamine diseases mentioned above. Since these are due to a mutation in a gene, as mentioned above, the predisposition for these diseases is usually hereditary. For this reason, they are collectively called "hereditary neurodegenerative disorders". However, it is a contentious issue whether or not for example schizophrenia even is a polyglutamine disease, since, unlike Huntington's disease, no polyglutamine-containing protein has been identified, thus far, that can be associated with the development of schizophrenia or is detected in schizophrenia patients at anomalous concentrations.

Moreover, polyglutamine diseases are rare diseases. Compared to Huntington's disease, neurodegenerative diseases that are not associated with polyglutamine are significantly more common, e.g. Alzheimer's disease 150-fold, Parkinson's disease 30-fold, and schizophrenia 100-fold more commonly (S. Prusiner 2001, New England Journal of Medicine 344: 1516f).

Although it is accepted that there exists a genetic disposition for schizophrenia, the causes appear to be multifactorial. This is indicated by the fact that even identical twins of a patient afflicted by schizophrenia have an only 50% risk of also being afflicted by schizophrenia (I. Gottesman and J. Shields 1982, Schizophrenia: the epigenetic puzzle, Cambride University Press, Cambridge; Kendler et al 1993, The Roscommon Family Study. I. Methods, diagnosis of probands, and risk of schizophrenia in relatives, Arch Gen Psychiatry 50 (7): 527).

The inventors then are the first to have found evidence indicating that the presence of misfolded proteins can serve as a diagnostic marker of schizophrenia or other neuropsychiatric diseases, such as for example, depression or bipolar affective disorders. In the process, it was postulated that misfolding is due to posttranslational causes and can not, or to a small degree only, be associated with sequence-related anomalies such as CAG repeats. For example, an error during protein biosynthesis or protein processing in the endoplasmic reticulum possibly that can be caused by defective processing enzymes, such as for example, translocon components or chaperones, can be responsible for misfolding. It is also conceivable that repair enzymes or proteases intended to repair and/or digest already misfolded proteins, are defective in function. It is also conceivable that certain posttranslational processing enzymes or proteases incorrectly modify an initially correctly folded protein such that it is produced excessively with incorrect folding.

In this context, the defective functions of the processing enzymes, repair enzymes and/or proteases can be caused by mutations in the respective genes or their interaction partners on the protein level which might explain a possible familial disposition for schizophrenia. In this context, possible candidates being discussed include the genes for the proteins, DISC-1, dysbindin, neuregulin 1, COMT, RGS4, metabotropic glutamate receptor-3, DMO, and G72 (P. Harrison & M. Owen 2003, Lancet 361:417f; P. Harrison and D. R. Weinberger 2005, Molecular Psychiatry 10:40-68).

According to the invention, the brain fractions from, for example schizophrenia, patients, are purified in a targeted fashion in order to isolate and enrich the posttranslationally misfolded proteins. In a preferred development, the purified fractions can be used to immunize, according to conventional technique, suitable animals (rabbits, mice, sheep, chickens) and, thus, obtain antibodies that bind specifically to these proteins.

Instead of an immunization, it is feasible to use recombinant ligand or antibody libraries, that are expressed, for example, in phages, to identify suitable anti-bodies or antibody fragments that bind specifically to the purified misfolded proteins and can be affinity-matured by mutagenesis under in vitro conditions after their identification.

A particularly preferred development provides the purification to be a purification step with ionic detergents. The purification of the brain fractions with ionic detergents serves to dissolve easily denatured proteins in the sample to be purified. However, misfolded proteins with a tendency to aggregate are not denatured by ionic detergents, in particular at temperatures between 0 and 10 degrees centigrade and, thus, do not remain in solution, i.e. pellet under the conditions of (ultra-)centrifugation and can, thus, be isolated in native form for the immunization.

In order to exclude that the schizophrenia-specific proteins are polyglutamine-containing proteins, the applicant subjected brain fractions that were isolated according to the invention from schizophrenia patients and healthy test subjects to a Western blot using the labeled antibody, MW1. Similar to the antibody, 1C2, that was used in WO 0026675, this antibody recognizes polyglutamine-rich epitopes in proteins and/or polyglutamine polymers. These experiments showed that polyglutamine-containing proteins were detected both in the brain fractions of schizophrenia patients and in those of healthy test subjects. However, no differences in the polyglutamine content were detected. The results are discussed below. The applicant concluded from these results that polyglutamine-containing proteins do not occur at elevated concentration in schizophrenia patients and thus cannot be used as diagnostic markers for schizophrenia.

As illustrated above, the purification of the brain fractions with ionic detergents serves to isolate misfolded proteins that are not denatured by these detergents. Moreover, a preferred development provides the purification step to be carried out at 0-10° C. since, at elevated temperatures, misfolded proteins can be denatured by ionic detergents also. It is particularly preferred to use a temperature of 0-5C in this purification step.

A further preferred development of the invention provides the ionic detergents that are used during the purification step to be used at a concentration between 0.2 and 2%. This measure again serves to prevent denaturation of the misfolded proteins, since these, at elevated concentration, can be denatured by ionic detergents also. Preferably a concentration is used in this purification step that ensures that the detergent does not yet form micelles ("critical micellar concentration", CMC).

Detergent molecules bind to proteins below the CMC, but form micelles above the CMC. A concentration below the CMC is more beneficial for the purification of misfolded proteins, since more detergent binds to undesired proteins and dissolves them, unlike misfolded proteins. The CMC differs between detergents. In addition, it must be taken into consideration that the CMC is also dependent on the pH value and temperature of the medium. Preferably, a concentration between 0.2 and 1% is used in this purification step.

A further preferred development provides the ionic detergent used in the purification step to be sarcosyl. The use of sarcosyl is preferred because it facilitates, on the one hand, the sufficient denaturation of undesired, correctly folded proteins, and, on the other hand, preserves the microaggregates of the misfolded proteins. This aggregation/solubility balance depends on the CMC of a detergent.

In contrast, the detergent, sodium dodecyl sulfate (SDS), acts too strongly denaturing and is therefore less well suited for the stated purpose.

It is particularly preferred to use sarcosyl at a concentration range between 0.3 and 0.42%. Under normal conditions, sarcosyl reaches its CMC at 0.45%.

It is particularly preferred to use an ultracentrifugation step at least 100,000×g in the purification step. Since the misfolded proteins are insoluble under the conditions mentioned, they are found in the pellet after ultracentrifugation, whereas other proteins remain in the supernatant.

A further preferred development provides the purification to include a purification step with β-sheet-binding substances, such as Congo red, thioflavine or β-sheet-binding peptides. If applicable, these substances can be immobilized in a chromatography column or similar. Since the secondary structure of the misfolded, schizophrenia-specific proteins comprises an increased fraction of β-sheet domains ("beta sheet"), the proteins thus sought can be specifically enriched by this means.

It is also preferred to provide a protease digestion step at a temperature between 0-10° C. in the purification. This step is also suitable for enriching misfolded schizophrenia-specific proteins since these possess increased resistance to proteases, such as proteinase K, at low temperatures due to their folding, whereas non-misfolded proteins are digested by proteases at these temperatures.

A further preferred embodiment provides the antibody to be a monoclonal antibody. In order to obtain monoclonal antibodies, a suitable animal is immunized first and then antibody-producing cells (e.g. B cells from the spleen) are removed from the immunized animal, fused with immortalized myeloma cells, and subjected to selection. The hybridoma cells thus obtained are then selected according to the specificity for the misfolded protein of the antibodies they produce. Instead of an immunization, it is feasible to use recombinant ligand or antibody libraries, that are expressed, for example, in phages, to identify suitable antibodies that bind specifically to the purified misfolded proteins and can be affinity-matured by mutagenesis under in vitro conditions after their identification.

In particular, monoclonal antibodies termed 7B2 and 9C9 can be used according to the invention. Hybridoma cells that can be used to produce the antibodies have been deposited in accordance with the Budapest agreement using the numbers, DSM ACC2713 and DSM ACC2714.

Monoclonal antibodies provide for higher specificity in the immunochemical detection reaction and, thus, improve the accuracy of, for example, a detection method. In this context, it is particularly preferred to provide the antibody to be a conformation-specific monoclonal antibody, i.e. an antibody that recognizes an epitope of a given protein only when it has a certain conformation, for example, exclusively when the epitope is present in a β-sheet conformation.

A particularly preferred development provides the antibody to be a recombinant antibody. In order to obtain an antibody of this type, DNA is isolated, e.g. from the spleen cells of immunized animals, and the paratope-coding cDNA fragments are cloned subsequently.

A further preferred development provides the antibody to be a blood-brain barrier-crossing antibody. The term, blood-brain barrier-crossing, means that the antibodies can cross the blood-brain barrier. In this context, various options are conceivable for rendering the blood-brain barrier such that it can be crossed by antibodies, for example the concomitant administration of suitable pharmaceuticals or hypertonic sugar solutions. On the other hand, the antibodies can as well be rendered capable of crossing the blood-brain barrier by molecular biological modifications, for example, by increasing their hydrophobicity or lowering their molecular weight or masking the antibody through a signal sequence that promotes the targeted transport across the blood-brain barrier.

Monoclonal antibodies possess very much higher specificity than polyclonal antibodies, but, like the former, also bear the risk of rejection reactions in therapeutic use. A further preferred development therefore provides the antibody to be a chimeric or a humanized antibody. In chimeric antibodies, the constant domains, for example, of mouse antibodies, are replaced by the corresponding constant domains of human antibodies by molecular biological means. In humanized antibodies, in addition, the basic frameworks of the variable domain are replaced by corresponding human sequences such that only the hypervariable regions responsible for antigen binding continue to be of murine origin. Antibodies, thus modified, cause only very weak and usually tolerable rejection reactions upon administration to the patient.

A further preferred development provides the antibody to be an antibody fragment. This can concern, for example, monovalent F(ab) fragments, such as are obtained, for example, after papain digestion of IgG antibody molecules, or bivalent F(ab)$_2$ fragments such as are obtained, for example, after trypsin digestion. Antibody fragments are easier to clone into chimeric antibodies or to combine with humanized or human sequences and/or signal sequences. Moreover, antibody fragments cause a weaker rejection reaction.

A further development can provide the antibodies according to the invention to be bound to a pharmaceutically active substance and/or, according to yet a further development, to an isotope or a radiolabeled molecule. The latter antibodies can be used, for example, in radioimmunotherapy or nuclear medicine diagnostic work-up.

Further, a method is provided for diagnosis of, for example, schizophrenia or depression or bipolar affective disorders by means of antibodies that bind to neuropsychiatric disease-specific proteins. In this context, the antibodies are contacted with a tissue or body fluid sample of a patient and antibody-protein complexes thus formed, if any, are detected. The potential presence of antibody-protein complexes is considered to be a positive finding of schizophrenia, depression or bipolar affective disorder in this context. The method is characterized in that one of the antibodies claimed above is used.

In this context, it has become evident that the antibodies produced by the applicant according to the invention bind specifically to proteins that are typical, for example, of schizophrenia. In order to provide evidence of this, the applicant carried out comparative immunochemical tests using brain homogenates from healthy and schizophrenia-afflicted test subjects. In this context, brain fractions from schizophrenia patients and healthy test subjects were subjected to a Western blot using the antibodies obtained according to the invention. As a result, the applicant detected immunoreactive bands that were detected only in the brain fractions from schizophrenia patients. Accordingly, the antibodies obtained according to the invention recognize proteins that occur only in schizophrenia patients. The results are discussed below.

A preferred development of the method provides the presence of antibody-protein complexes to be detected by means of ELISA, Western blotting or immuno-coupled fluorescence methods. However, any other suitable method capable of detecting the binding of antibodies and/or other probe molecules to antigens, is conceivable as well.

Since, in the case of neuropsychiatric diseases, in particular schizophrenia, but also in depression or bipolar affective disease, misfolded proteins are presumably detectable in tissue or body fluid samples of a patient long before the actual onset of disease, the method according to the invention is also suitable for detection of a possibly present disposition for the respective neuropsychiatric disease, i.e. for schizophrenia, but also for depression or bipolar affective disease. Accordingly, a preferred development of the method according to the invention provides the positive finding to be a diagnosed predisposition and/or a positive diagnosis for a specific neuropsychiatric disease, thus in particular for schizophrenia or a subgroup of schizophrenia, and/or depression or bipolar affective disorder.

A particularly preferred development of the method according to the invention provides the body fluid sample to be tested to be liquor, urine, blood or serum. It can be presumed that disease-specific misfolded proteins occur not only in the brain matrix, but also in body fluids of a patient suspected of schizophrenia, but also in patients suspected of depression or bipolar affective disease. This applies in particular to the liquor (cerebrospinal fluid) that is in constant contact with the brain and of which samples can be obtained by tapping the spinal canal as part of the clinical routine with no risk or pain.

However, the present invention is not limited to a method for diagnosis of schizophrenia, depression or bipolar affective disorder, but also extends to the use, for example, of the antibodies according to the invention in the production of a pharmaceutical composition for treatment of such diseases.

This concerns compositions that can be administered to a patient, in particular, in a blood-brain barrier-crossing form. In particular, the antibodies claimed above are used in order for the antibodies, after they reach the brain, to bind to, for example, schizophrenia-specific misfolded proteins and prevent, for example, their aggregation with other misfolded proteins.

A particularly preferred development provides the administered antibodies to be coupled to pharmaceutically active substances. Substances of this type can, for example, be markers that mark the antibody-bound protein such that it can be digested by a protease or phagocytosed by a microglia cell. However, this can also concern substances that visualize the antibody-labeled proteins in imaging procedures (NMR, CT). It is also conceivable to use antibodies coupled to radioactively labeled substances.

Another variant provides the production of compositions through the use of small-molecule, blood-brain barrier-crossing agents that recognize the same sites as the antibodies claimed above that are directed against misfolded, schizophrenia-specific proteins. In this context, the antibodies claimed above serve as templates for definition of a surface structure on the misfolded proteins for which small-molecule agents are then identified in chemical libraries by means of common techniques that are collectively called "molecular design", whereby said small-molecule agents reproduce at least a similar surface structure on the misfolded protein as the antibody that is used. The antibodies can, for example, be molecules obtained by cloning, whose cDNA was identified from a molecular biological library of human antibodies or peptides.

Preferably, these small-molecule agents are organic molecules that bind specifically to one of the epitopes of schizophrenia-specific proteins that are recognized by one of the antibodies claimed above. Such agents are also called "small molecular drugs". These can be natural substances just as well as molecules produced by synthesis. Small molecular drugs are advantageous as compared to anti-bodies or antibody fragments in that they can be administered by the oral route, rarely elicit immunological rejection reactions, and can cross the blood-brain barrier more easily due to their low molecular weight.

It is particularly preferred for these small molecule agents to comprise multiple ligands that are connected to each other by spacers, whereby the ligands each bind specifically to various, non-overlapping epitopes of schizophrenia-specific proteins that are recognized by the antibodies claimed above. Such agents are also called "composite molecules" and are advantageous, in particular, as they possess much higher affinity for the protein to be bound. Accordingly, the affinity of a molecule for the protein to be bound multiplies with each new ligand added.

A final variant provides the production of pharmaceutical compositions through the use of immunogenic substances that elicit an immune response such that the immune system of the patient forms antibodies against misfolded, e.g. schizophrenia-specific, proteins.

These substances can, for example, be schizophrenia-specific proteins or proteins that are specific for other neuropsychiatric diseases such as depression or bipolar affective disorder, such as can be isolated using one of the purification methods claimed above or their equivalents produced by recombinant technique. In order to remove any pathogenicity these proteins may have, it may under some circumstances be necessary to subject them to a suitable treatment prior to administration. In addition, these substances can, for example, be fragments of the schizophrenia- (or, if applicable, depression- or bipolar affective disease-)specific proteins that are defined by means of the antibodies claimed above, whereby said fragments only contain the immunogenic regions, but are no longer pathogenic.

DETAILED DESCRIPTION OF THE INVENTION

The invention shall be illustrated in the following on the basis of examples:

A. Isolation of Misfolded Proteins

Solutions or Buffers Used (Sterile-Filtered):

VRL-buffer: 50 mM HEPES, pH 7.5, 250 mM sucrose, 5 mM $MgCl_2$, 100 mM $KCH_3COO$, 2 mM PMSF, protease inhibitor tablets, "Complete EDTA-free" (Roche 1873580)

High-sucrose buffer: 50 mM HEPES, pH 7.5, 1.6M sucrose, 100 mM KAc ($KCH_3COO$), 0.5% Triton-X-100, 1 mM PMSF#

High-salt buffer: 50 mM HEPES, pH 7.5, 1M NaCl, 10 mM MgCl2, 100 U/ml DNAse I

Sarcosyl buffer: 50 mM HEPES, pH 7.5, 0.5% sarcosyl

Other Buffers:

A. 50 mM HEPES pH 7.5, 300 mM NaCl, 250 mM sucrose, 5 mM EDTA, 5 mM GSH, 1% NP-40, 0.2% sarcosyl.
B. 50 mM HEPES pH 7.5, 1.5 M NaCl, 250 mM sucrose, 5 mM EDTA, 5 mM GSH, 1% NP-40.
C. 50 mM Tris pH 8, 250 mM sucrose, 5 mM $MgCl_2$, 5 mM GSH, 1% NP-40.
D. 50 mM HEPES pH 7.5, 5 mM EDTA, 5 mM GSH, 1% NP-40.
E. 50 mM HEPES pH 7.5, 2.3 M sucrose, 5 mM EDTA, 5 mM GSH, 1% NP-40. Adjust sucrose concentration using Puffer D.
F. 50 mM HEPES pH 7.5, 150 mM NaCl, 250 mM sucrose, 5 mM EDTA, 5 mM GSH, 2×PIs.

Abbreviations: Pis=protease inhibitor cocktail (Roche); PMSF=phenyl-methylsulfonyl fluoride (Sigma), GSH=reduced glutathione (Sigma)

Protocol 1: "Preparation of the insoluble protein fraction (misfolded proteome) from a 10% brain homogenate"

1. Shock-frozen brain fractions from brain regions BA8, BA9, and BA23, BA24 of deceased patients, who had been diagnosed with schizophrenia when they were alive, were used. BA8, BA9, BA23, and BA24 refer to so-called Brodmann areas and correspond to certain neuronal centers in the neocortex.

2. Weigh out brain samples on dry ice and homogenize in the corresponding volume of VRL buffer. Store at −80° C.

3. Thaw the homogenate on ice and centrifuge in the presence of 0.5% Triton-X-100 in 2 ml micro-reaction vessels at 20,000 g at 4° C. for 20 min. Collect supernatant and resuspend pellet in the same volume of VRL buffer plus Triton.

4. Repeat the centrifugation as above. Add supernatant to first supernatant, store 500 µl separately at −80° C.

5. Dissolve pellets in a total of 4 ml high sucrose buffer. Subject to ultracentrifugation in ultra-clear centrifuge tubes 5 ml at 130,000 g, 4° C., 45 min (Beckmann MLS-50, 40,000 rpm), collect supernatant, freeze supernatant lipid layer in separate microreaction vessel.
6. Resuspend pellet in another 4 ml of high-sucrose buffer and repeat centrifugation as above. Add supernatant to the first supernatant. Storage at −20° C.
7. Dissolve pellet in 4 ml high-salt buffer, incubate over-night at 4° C. Subject to ultracentrifugation in ultra-clear centrifuge tubes 5 ml at 130,000 g, 4° C., 45 min (Beckmann MLS-50, 40,000 rpm), collect supernatant, and resuspend pellet again in high-salt buffer (without DNAse). Upon need, take up pellet with an insulin syringe equipped with a 0.6 mm to 0.4 mm-cannula.
8. Second centrifugation as above. Add supernatant to first supernatant, store 500 µl separately at −80° C. Storage at −20° C.
9. Dissolve pellet in 200 µl sarcosyl buffer. For this purpose, mince pellet in 100 µl buffer using the pipette tip and then transfer to a 0.5 ml microreaction vessel. Rinse vessel and pipette tip with another 100 µl sarcosyl buffer and add to first 100 µl. Use insulin syringe and 0.4 mm-cannula to dissolve pellet. Incubate in rotator at 4° C. for approx. 1 h. Possibly, after approx. half of this time, rehomogenize using an insulin syringe.
10. Ultracentrifugation in microreaction vessel (Beckmann 357448 polyallomer tubes with snap-on caps) whose weight was determined on an analytical scale, at 112,000 g, 4° C., 45 min) (Beckmann TLA-55, 50,000 rpm). Collect supernatant and wash again in 200 µl sarcosyl buffer. Resuspension and centrifugation as above.
11. Collect supernatant and determine the weights of the pellets. Storage at −80° C.

Protocol 2 "Preparation of the insoluble protein fraction (misfolded proteome) from a 10% brain homogenate"
1. Homogenize the brain fragment (e.g. 0.3-0.4 gr=1 vol) at 5% (w/v) in buffer A (plus 2×Pls, 1 mM PMSF) and centrifuge at 1,800×g, 30 min, 4° C. Wash the pellet in buffer A (5 ml [15 vol] washing volume) and continue the work-up.
2. Suspend the pellet in buffer B (10 ml [30 vol] washing volume; and add 1 mM PMSF and 0.2% sarcosyl), centrifuge (1,800×g, 30 min, 4° C.), and wash once in buffer B (5 ml [15 vol] washing volume).
3. Continue the work-up of the pellet after washing in buffer C (5 ml [15 vol] washing volume), then resuspend thoroughly in buffer C (5 ml [15 vol] washing volume; plus 2×Pls, 1 mM PMSF, benzonase, and DNAseI, 40 U/ml each) and shake for 30 minutes at 37° C. Subsequently, shake the same mixture over-night at 4° C. and centrifuge the next morning (1,800×g, 30 min, 4° C.).
4. Subsequently, wash the pellet in buffer A (plus 1 mM PMSF, (5 ml [15 vol] washing volume), centrifuge (1,800×g, 30 min, 4° C.), and resuspend in buffer D. After successful resuspension, add sucrose to adjust the final sucrose concentration to 1.6 M (70% of the sucrose concentration of buffer E).
5. The suspension obtained under 4) is then placed at a ratio of 4:1 on a bed of 1 ml of buffer E and centrifuged in the ultracentrifuge at 45,000 rpm for 45 minutes using the MLS-50 rotor (approx. 120,000×g).
6. Remove the interphase between the sucrose phases with a pipette (approx. 1 ml) and dilute with buffer D at a ratio of 1:4. Then place this suspension again on 1 ml 70% buffer E and centrifuge for 45 minutes at 45,000 rpm in the MLS-50 rotor (approx. 120,000×g). Take up the resulting pellet (0.1 ml) in buffer F.
7. The resulting pellet ("insoluble protein fraction") is subsequently used both for immunization and for the dot blots and SDS-PAGE/Western blot.

All steps are carried out at 4° C., and/or on ice. The centrifugation in steps 1-4 is carried out with a tabletop centrifuge at 1,800×g, 30 minutes at 4 degrees centigrade.

B. Antibody Production a) Polyclonal Antibodies

Chickens, rabbits, and mice (BALB/c) are immunized with approx. 500-1000 µg/100 µl of pellets pooled from four schizophrenia patients. In this context, RIBI (Sigma) is added to the (aggregated) antigen as adjuvant. The animals are boostered twice with an interval of 3 weeks. The immune response is investigated two weeks after the final booster. In the case of chickens, eggs are collected one week after the booster, starting after the first booster, and antibodies (IgY) are isolated from the egg yolk using standard methods.

b) Monoclonal Antibodies

In order to obtain monoclonal antibodies, a suitable animal is immunized as described and antibody-producing cells (e.g. B cells from the spleen) are removed from the immunized animal in known fashion (G Köhier, C Milstein 1975, Continuous cultures of fused cells secreting antibody of predefined specificity. Nature, 256, 495-497), fused with immortalized myeloma cells, and subjected to selection. The hybridoma cells obtained are then selected with regard to the specificity for the misfolded protein of the antibodies they produce.

The monoclonal antibodies 7B2 and 9C9 were produced as follows: Insoluble misfolded proteins purified from frozen pieces of brain (cortex, BA8) of 15 schizophrenia patients were pooled and injected subcutaneously into prion protein (PrP) knockout mice for immunization using RIBI as adjuvant. PrP knockout mice were used since they have been used successfully for generating conformation-specific monoclonal antibodies before, and they are also used preferably in the present invention for generating conformation-specific mABs against antigens other than PrP. The mice were boostered twice, after an interval of three weeks each; ten days after the final booster, the mice received an intraperitoneal booster on two consecutive days, and the spleen was removed for fusion on the third day. The spleen cells (splenocytes) were fused with the myeloma cells according to standard methods to obtain resulting hybridoma cells.

C: Immunological Characterization

In general, the antibodies obtained were used to investigate brain homogenates of normal, schizophrenic, depressive, and bipolar affective disorder patients by means of Western blotting and/or dot blotting.

The results are shown in the figures.

Figure 1:
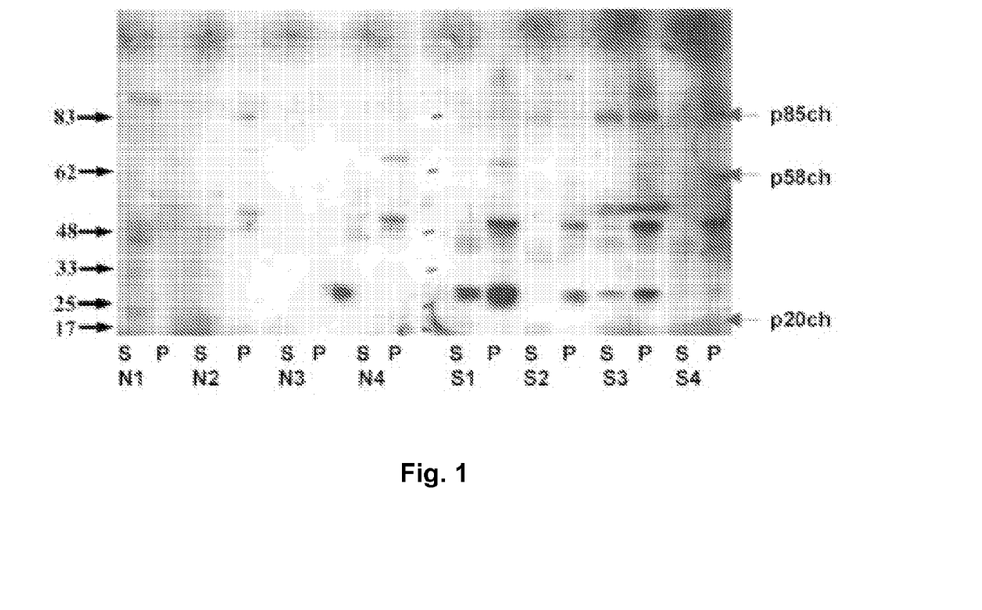
FIG. 1 shows a Western blot of biochemically fractionated pellet or first supernatant (after sarcosyl incubation) of brain homogenates of normal or schizophrenic patients after biochemical fractionation for poorly soluble, sarcosyl-resistant protein aggregates (antibody: chicken IgY).

In the figures:

S=first supernatant, P=pellet, N1-N4=brain of healthy subjects, S1-S4=brain of schizophrenia patients. The arrows (p85ch, p58ch, p20ch) refer to immunoreactive bands that occur specifically in schizophrenia patients only and, thus, constitute biological markers. The arrows on the left side indicate molecular weights.

Figure 2:
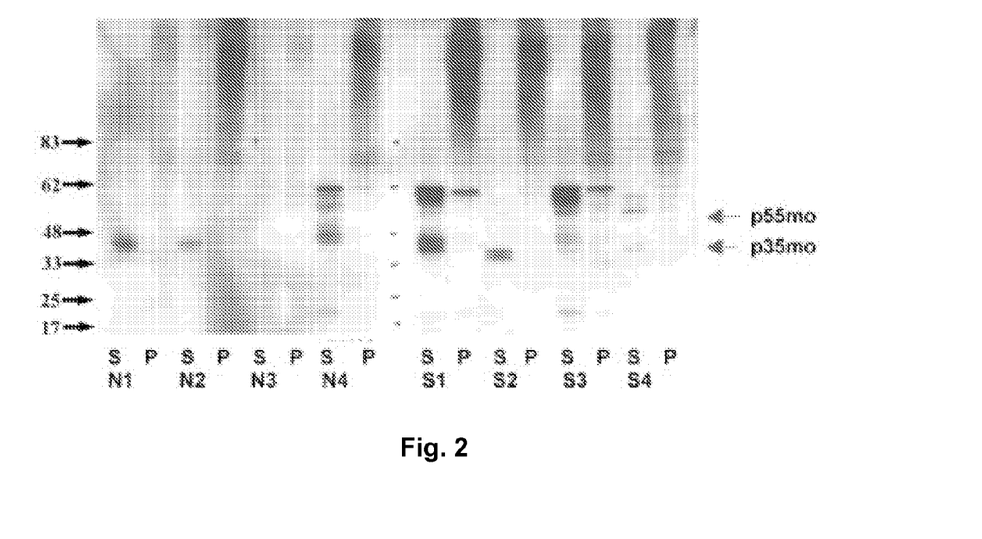
FIG. 2 shows a Western blot of biochemically fractionated pellet or first supernatant of brain homogenates of normal or schizophrenic patients after biochemical fractionation for poorly soluble, sarcosyl-resistant protein aggregates (antibody: mouse serum).

S=first supernatant, P=pellet, N1-N4=brain of healthy subjects, S1-S4=brain of schizophrenia patients. The arrows refer to immunoreactive bands that occur specifically in schizophrenia patients only and, thus, constitute biological markers thereof (p55mo, p35mo). The arrows on the left side indicate molecular weights.

Figure 3A:
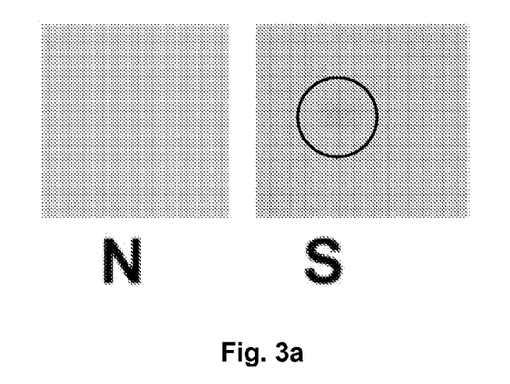
FIG. 3a shows a dot blot using monoclonal antibody RC1 under non-denaturing conditions of a pool of sarcosyl-resistant pellet (fraction X) of pooled normal brain (N; BA9) and pooled schizophrenia brain (S; BA9).

The monoclonal conformation-specific antibody, RC1, that recognizes with high conformational specificity the native surface structure of a protein that is specifically present in schizophrenia, was used as antibody.

Figure 3B:
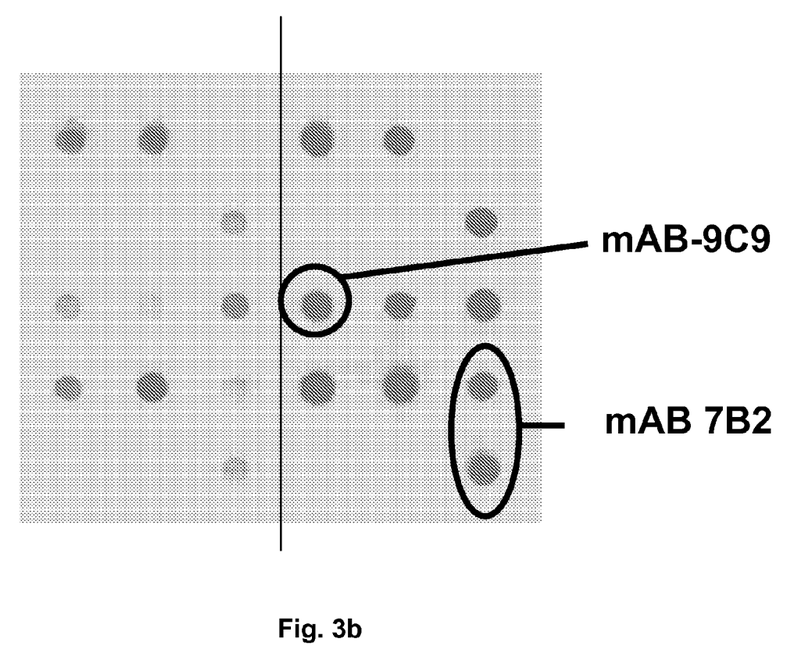

FIG. 3b shows a dot blot assay with monoclonal antibodies 7B2 and 9C9. The monoclonal antibodies, 7B2 and 9C9, were obtained and tested according to the following screening: the cell culture supernatants of approx. 3,000 hybridoma cells were screened using a dot blot assay and a specialized apparatus (ELIFA apparatus; Pierce, USA) with a 96-well format. In the process, identical quantities of the pooled insoluble proteins (purified according to protocol 1) from schizophrenia patients and normal people were applied to nitrocellulose in parallel, the membrane was blocked with 5% non-fat dry milk in TBST (Tris-buffered salt solutions containing Tween), and the cell culture supernatants in the wells of the ELIFA apparatus were incubated on the dots at room temperature for 2 h. The membrane was washed and incubated for one hour with a secondary antibody (anti-mouse IgG/M) to which peroxidase was covalently coupled. The blot was then washed, ECL substrate was added, and the blot was developed on hyperfilm (Amersham). The results are shown in FIG. 3b. The hybridoma cells of the supernatants that reacted much more strongly or exclusively with the insoluble proteins of the schizophrenia brains (black) were picked and subcloned multiply. Then, a substantial quantity of supernatant in serum-free medium (PFHM; Gibco, USA) was produced and used in the subsequent tests. Two antibodies termed 7B2 and 9C9 proved to be particularly well suited.

Figure 4:
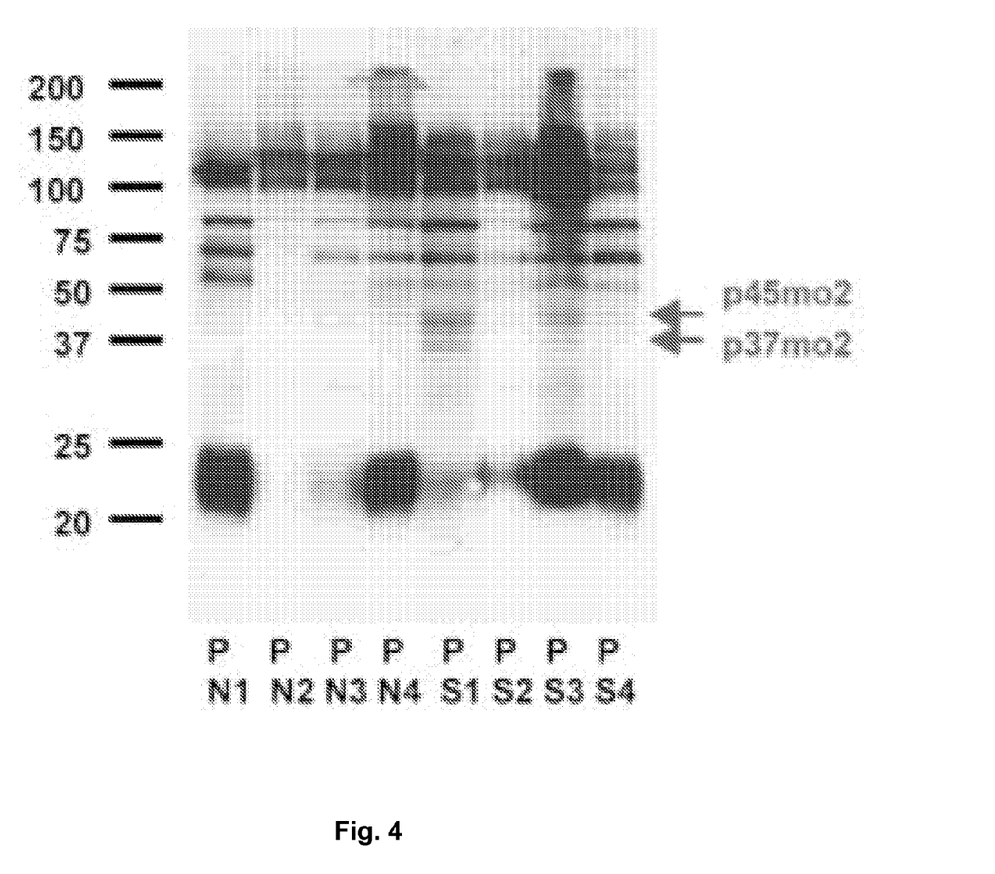
FIG. 4 shows a Western blot of biochemically fractionated pellet of brain homogenates of normal or schizophrenic patients.

The homogenates were purified according to protocol 1. Antibodies were from mouse serum. P=pellet, N1-N4=brain of healthy subjects, S1-S4=brain of schizophrenia patients. The arrows indicate immunoreactive bands that occur specifically in schizophrenia patients only and thus constitute biological markers (p45mo2, p37mo2). Antibodies: mouse serum.

FIG. 5 a) shows a Western blot of biochemically fractionated pellet of brain homogenates of normal or schizophrenic patients.

Figure 5A:
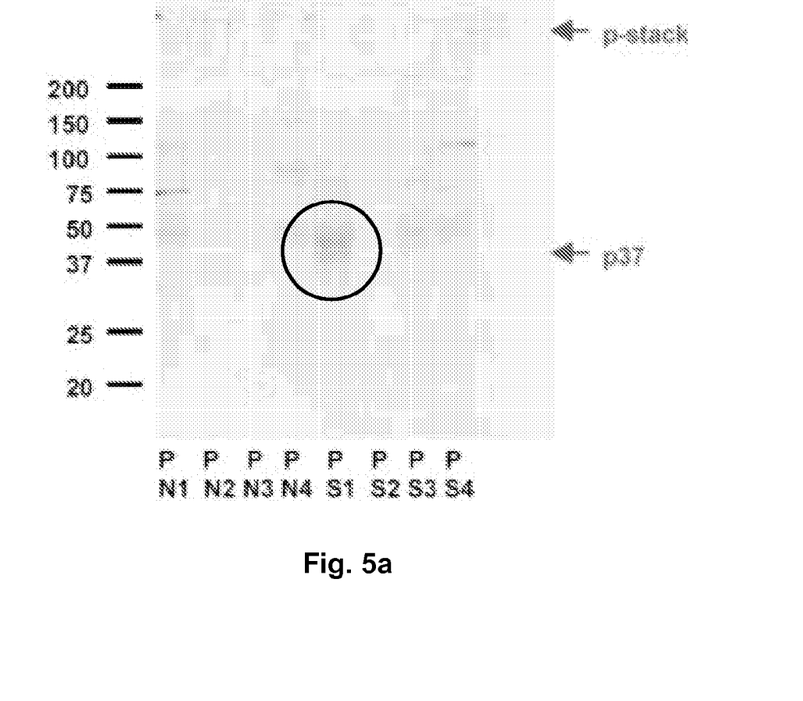

The homogenates were purified according to protocol 1. The monoclonal antibody, AK SX16.3, was used as antibody. P=pellet, N1-N4=brain of healthy subjects, S1-S4=brain of schizophrenia patients. The arrows indicate immunoreactive bands that occur specifically in schizophrenia patients only and thus constitute biological markers (p37, p-stack). p-stack is an immunoreactivity from the well. This corresponds to insoluble proteins that had been taken up when the gel was loaded, but were not transported in the gel due to their insolubility. Some of p-stack dissolved and forms p37.

FIG. 5 b) shows a Western blot of biochemically fractionated pellet of brain homogenates of normal or schizophrenic patients from the region, BA9.

Figure 5B:
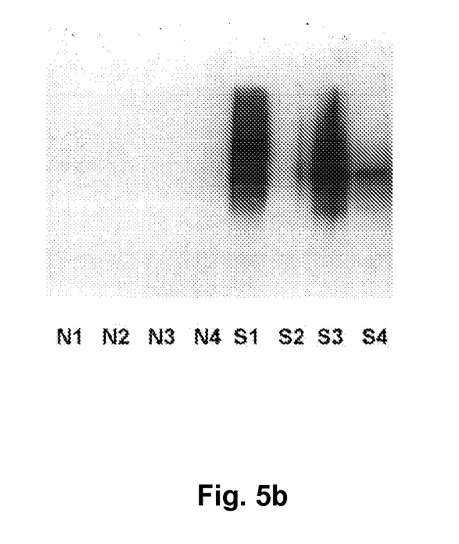

The homogenates were purified according to protocol 1. The monoclonal antibody, AK 7B2, was used as antibody. P=pellet, N1-N4=brain of healthy subjects, S1-S4=brain of schizophrenia patients. It is evident that AK 7B2 shows immunoreactivity only in the case of schizophrenia brains.

Figure 6:
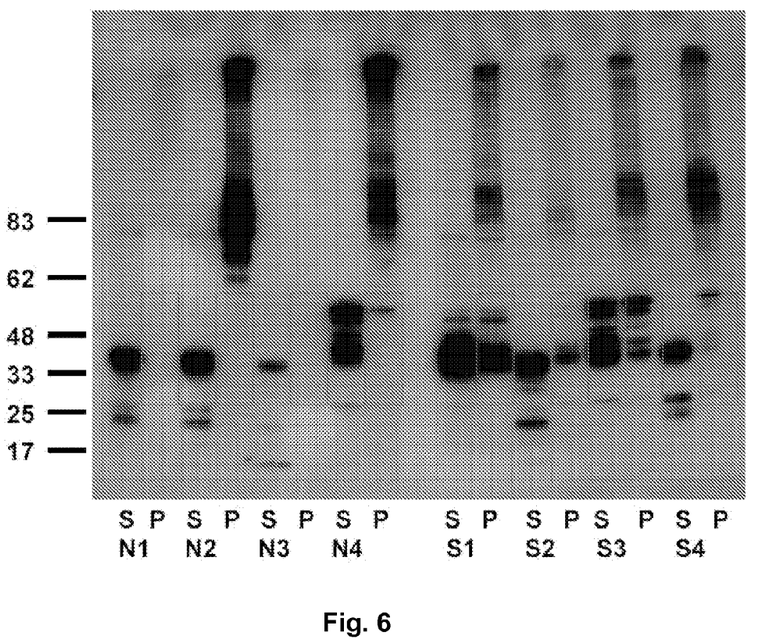
FIG. 6 shows a Western blot of biochemically fractionated pellet and/or the first supernatant of brain homogenates of normal or schizophrenic patients.

The homogenates were purified according to protocol 1. Antibodies were from rabbit antiserum. S=first supernatant, P=pellet, N1-N4=brain of healthy subjects, S1-S4=brain of schizophrenia patients. Although there are no immunoreactive bands that occur exclusively in schizophrenics, but not in healthy people, it is clearly evident that, in the marked rectangles, immunoreactivity is present only in schizophrenics. This means that insoluble proteins pellet in the molecular region below 60 kD exclusively in schizophrenics.

Figure 7:
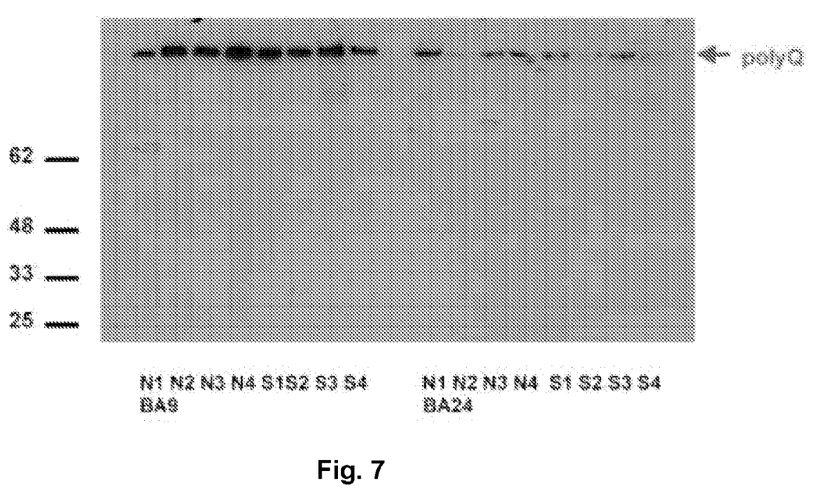
FIG. 7 shows a Western blot of biochemically fractionated pellet and/or the first supernatant of brain homogenates of normal or schizophrenic patients.

The homogenates were purified according to protocol 1. The monoclonal antibody, MW1, recognizing polyglutamine-containing ("polyQ") epitopes [Ko et al., 2001, Brain Research Bulletin 56:319f] was used as antibody. S=first supernatant, P=pellet, N1-N4=brain of healthy subjects, S1-S4=brain of schizophrenia patients. BA9 and BA24 denote various brain regions according to Brodman. Polyglutamine-containing bands are evident at the upper edge of the gel and correspond to SDS-resistant polyglutamine multimers pelleted in the well that had been taken up during the loading of the gel, but were not transported in the gel due to their relative insolubility. However, no difference between normal and schizophrenia patients can be detected. Therefore, this is evidence to indicate that polyglutamine-containing proteins are not schizophrenia-specific.

Figure 8:
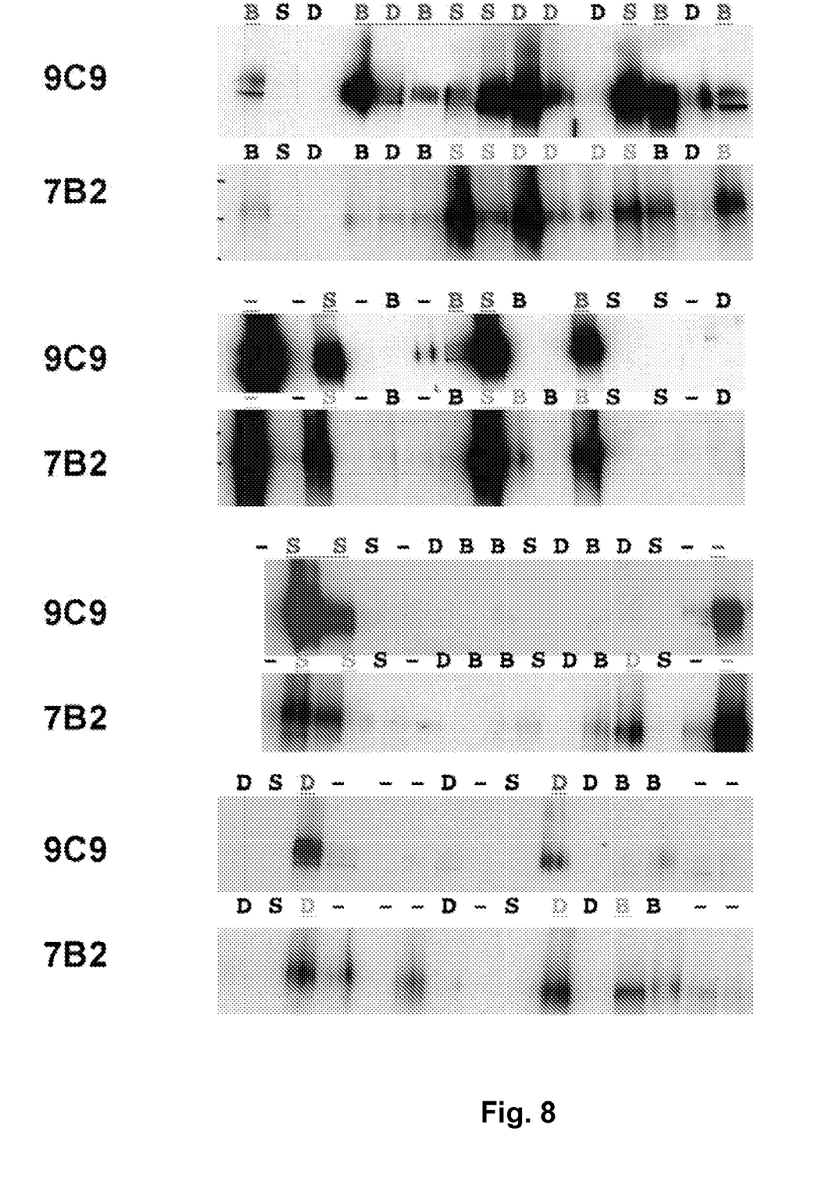
FIG. 8 shows a Western blot using 7B2 and 9C9 against insoluble protein fractions B8 of the SMRI Consortium Collection (SMRI).

The monoclonal antibodies, 7B2 and 9C9, were tested on the Western blot (WB) against the insoluble protein fractions of BA8 brain homogenates of patients afflicted by schizophrenia (the same that were used for immunization), depression, bipolar disorder, and normal controls. The results are shown in FIG. 8. The insoluble protein fraction of the individual brains was separated by means of SDS-PAGE and shown in the WB. The assessment was made blinded, i.e. without the above-mentioned diagnoses of the individual brains being known. A positive assessment was made only in the case of bands possessing sufficient immunoreactivity. With regard to mAB 9C9, statistical analysis by means of crosstabs/Pearson chi-square analysis showed that the immunoreactive bands assessed as positive recognized the following: 2 (of 15) normal controls; 5 (of 15) depressive patients, 7 (of 15) bipolar patients, and 7 (of 15) schizophrenics. Thus, 9C9 afforded significant recognition of diseased vs. normal ($p=0.042$), schizophrenic vs. normal ($p=0.046$), and bipolar vs. normal ($p=0.046$). SPSS (version 11.0 on Apple G4) was used for statistical analysis.

With regard to mAB 7B2, statistical analysis by means of crosstabs/Pearson chi-square analysis showed that the immunoreactive bands assessed as positive recognized the following: 2 (of 15) normal controls; 6 (of 15) depressive patients, 5 (of 15) bipolar patients, and 7 (of 15) schizophrenics. Thus, 7B2 afforded significant recognition of schizophrenic vs. normal ($p=0.046$), but not of bipolar vs. normal ($p=0.195$) or diseased vs. normal ($p=0.058$). SPSS (version 11.0 on Apple G4) was used for statistical analysis.

Figure 9:
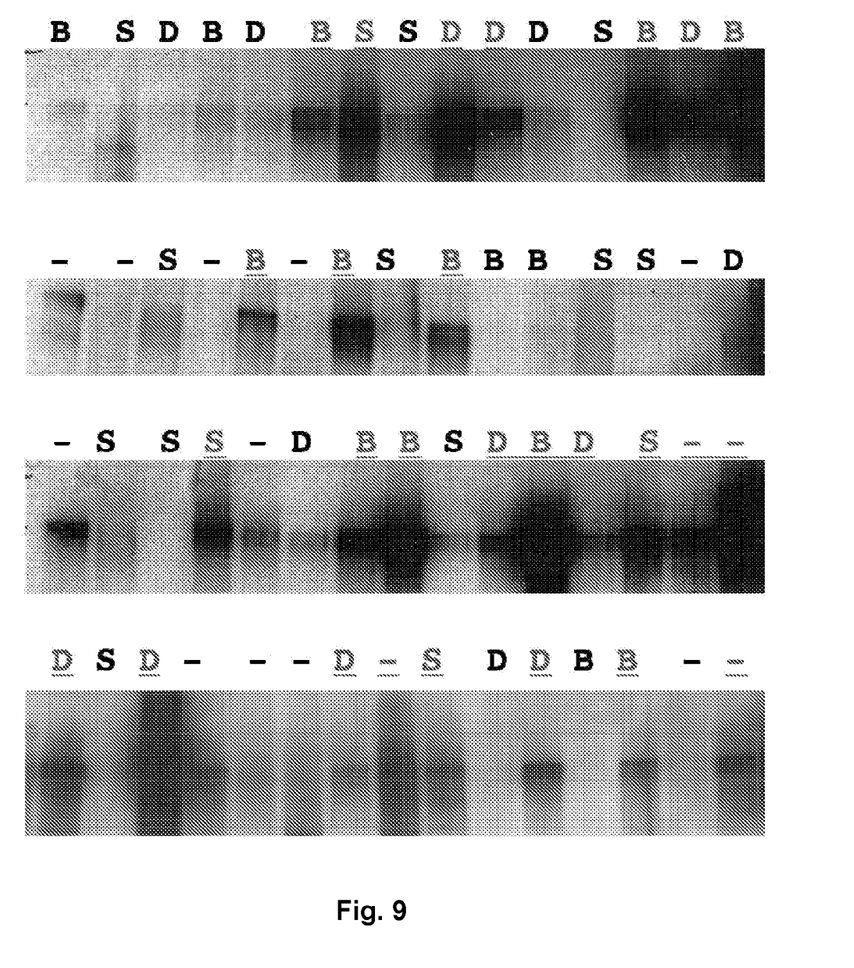
FIG. 9 shows a Western blot of 7B2 against insoluble protein fractions from BA23 (SMRI)

Moreover, 7B2 was tested on the Western blot (image 3) against the insoluble protein fractions of BA23 brain homogenates, i.e. from a different brain region, of patients afflicted by schizophrenia, depression, bipolar disorder, and normal controls. A positive assessment was made only in the case of bands that possessed sufficient immunoreactivity and, in particular, included the second, somewhat smaller, band.

With regard to mAB 7B2, statistical analysis by means of crosstabs Pearson chi-square analysis showed that the immunoreactive bands assessed as positive recognized the following: 4 (of 15) normal controls; 9 (of 15) depressive patients, 10 (of 15) bipolar patients, 4 (of 15) schizophrenics. Thus, 7B2 afforded significant recognition of bipolar vs. normal ($p=0.028$), but not of schizophrenia vs. normal ($p=1$) or diseased vs. normal ($p=0.09$). SPSS (version 11.0 on Apple G4) was used for statistical analysis.

Comparison of the data from FIG. 8 and FIG. 9 therefore shows that the 7B2 antigen is insoluble in the BA8 region (prefrontal cortex) and allows a distinction to be made between schizophrenia brains and normal brains in this region, but that this does not apply in another brain region (BA23, posterior cingulum). In this site, 7B2 cannot distinguish between schizophrenia brains and normal brains, but between bipolar brains and normal brains, which it does not afford in the BA8 region.

These results reflect the fact that there are overlaps in the biological cause of schizophrenia and bipolar disorder that are reflected in the different solubility of the antigen of 7B2 in various brain regions. These differences might be caused by the differential presence of certain cell types or a certain extracellular milieu. In summary, it can be concluded that mABs 7B2 and 9C9 are suitable for specific recognition of neuropsychiatric diseases, specifically of schizophrenia, bipolar disorder, and depression, by means of brain homogenates.

Deposition of Biological Material:
Hybridoma cells producing the antibodies, 7B2 and 9C9, have been deposited with "Deutsche Sammlung von Mikroorganismen und Zellkulturen GmbH, Mascheroder Weg 1 b, D38124 Braunschweig", in compliance with the Budapest agreement as follows:
1. Hybridoma cells (antibody 7B2): DSM ACC2713, deposition date: 26.01.2005.
2. Hybridoma cells (antibody 9C9): DSM ACC2714, deposition date: 26.01.2005.

The invention claimed is:

1. A monoclonal antibody produced from the hybridoma cell line deposited as DSM ACC2714 (mAB 9C9).

2. The monoclonal antibody according to claim 1, wherein the monoclonal antibody recognizes misfolded proteins that are associated with schizophrenia.

3. The monoclonal antibody according to claim 1, wherein the monoclonal antibody recognizes misfolded proteins that are associated with depression.

4. The monoclonal antibody according to claim 1, wherein the monoclonal antibody recognizes misfolded proteins that are associated with bipolar affective disorder.

5. The monoclonal antibody according to claim 1, wherein the monoclonal antibody has been modified to be a blood-brain barrier-crossing monoclonal antibody.

6. A binding fragment of a monoclonal antibody produced from the hybridoma cell line deposited as DSM ACC2714 (mAB 9C9), wherein said binding fragment recognizes misfolded proteins that are associated with neuropsychiatric diseases selected from the group consisting of schizophrenia, depression and bipolar affective disorder.

7. The monoclonal antibody according to claim 1, wherein the monoclonal antibody is coupled to a pharmaceutically active substance.

8. The monoclonal antibody according to claim 1 wherein the monoclonal antibody is coupled to an isotope or a radioactive labeled molecule.

9. A pharmaceutical preparation in a blood-brain barrier-crossing form comprising the monoclonal antibody according to claim 1.

10. The pharmaceutical preparation according to claim 9, wherein the monoclonal antibody is coupled to a pharmaceutically active substance.

11. The pharmaceutical preparation according to claim 9, wherein the monoclonal antibody is coupled to an isotope or a radioactively labeled molecule.

12. The binding fragment according to claim 6, wherein the binding fragment is cloned into a chimeric antibody or is combined with humanized or human sequences.

13. The binding fragment according to claim 6, wherein the binding fragment is coupled to a pharmaceutically active substance.

14. The binding fragment according to claim 6, wherein the binding fragment is coupled to an isotope or a radioactive labeled molecule.

15. A method for diagnosing a neuropsychiatric disease selected from the group consisting of schizophrenia, depression and bipolar affective disorder using a monoclonal antibody, or binding fragment thereof, produced from the hybridoma cell line deposited as DSM ACC2714 (mAB 9C9) that recognizes misfolded proteins that are associated with said neuropsychiatric disease, said method comprising:
   a) contacting a tissue or body fluid sample of a patient with said monoclonal antibody or binding fragment thereof; and
   b) detecting any antibody-protein complexes thus formed, wherein the presence of said antibody-protein complexes is considered to be a positive finding for said neuropsychiatric disease.

16. The method according to claim 15, wherein the presence of antibody-protein complexes is detected by means of ELISA, Western blotting or immuno-coupled fluorescence methods.

* * * * *